United States Patent [19]
Hoffman et al.

[11] Patent Number: 6,048,696
[45] Date of Patent: Apr. 11, 2000

[54] METHOD OF IDENTIFYING NUCLEIC ACID MOLECULES

[75] Inventors: Leslie M. Hoffman; Gregory A. Hawkins, both of Madison, Wis.

[73] Assignee: Epicentre Technologies Corporation, Madison, Wis.

[21] Appl. No.: 09/078,290

[22] Filed: May 13, 1998

[51] Int. Cl.$^7$ .............................. C12Q 1/68; C12P 19/34; C07M 21/02; C07K 13/00

[52] U.S. Cl. ................................. 435/6; 435/5; 435/91.1; 435/91.2; 435/91.5; 435/91.21; 435/18; 530/350; 536/23.1; 536/24.3

[58] Field of Search .................................. 435/5, 6, 91.1, 435/91.2, 91.5, 91.21, 18; 530/350; 536/23.1, 24.3

[56] References Cited

U.S. PATENT DOCUMENTS

| | | |
|---|---|---|
| 4,849,077 | 7/1989 | Rosenthal, et al. . |
| 4,950,665 | 8/1990 | Floyd .................................. 514/222.2 |
| 5,035,996 | 7/1991 | Hartley ........................................ 435/6 |
| 5,427,911 | 6/1995 | Ruano . |
| 5,447,839 | 9/1995 | Manos et al. ............................... 435/5 |
| 5,571,666 | 11/1996 | Floyd et al. ................................. 435/2 |
| 5,705,627 | 1/1998 | Manos et al. ........................... 536/24.3 |

FOREIGN PATENT DOCUMENTS

| | | |
|---|---|---|
| EP 0 329 311 A1 | 8/1989 | European Pat. Off. . |
| 0684315 A1 | 3/1995 | European Pat. Off. . |
| WO 97/06752 | 3/1995 | WIPO . |
| WO 96/23895 | 8/1996 | WIPO . |
| WO 97/03210 | 1/1997 | WIPO . |
| WO 97/41259 | 11/1997 | WIPO . |

OTHER PUBLICATIONS

Bessmans, et al., "Enzymatic Synthesis of Deoxyribonucleic Acid. III. The Incorporation of Pyrimidine and Purine Analogues into Deoxyribonucleic Acid," *Proc. Natl. Acad. Sci. USA*, 44(7):633–640 (1958).

Bjørås, M., et al., "Opposite base–dependent reactions of a human base excision repair enzyme on DNA containing 7,8–dihydro–8–oxoguanine and abasic sites," *The EMBO Journal*, 16:6314–6322 (1997).

Brow, M.D., et al., "Differentiation of Bacterial 16S rRNA Genes and Intergenic regions and *Myobacterium tuberculosis* katG Genes by Structure–Specific Endonulease Cleavage," *Journal of Clinical Microbiology*, 34:3129–3137 (1996).

Cannon, et al., "5–hydroxymethylcytosine DNA Glycosylase Activity in Mammalian Tissue," *Biochem, Biophys, Res. Commun*. 151(3):1173–1179 (1988).

Castaing, B., et al."Cleavage and binding of a DNA fragment containing a single 8–oxoguanine by wild type and mutant FPG proteins," *Nucleic Acids Research*, 21:2899–2905 (1993).

Cook, et al., "Enzyme–labeled Oligonucleotides for the Detection of $\alpha_1$–antitrypsin Deficiency: Optimization of Enzyme Activity for Single Point Mutation Detection," *Ann. Cain. Biochem*, 32:91–93, 1995.

Cotton, "Current Methods of Mutation Detection," *Mutation Research*, 285:125–144 (1993).

Cox, D.W., "$\alpha_1$–antirypsin Deficiency," *The Metabolic Basis of Inherited Disease*, 6th Ed., Shriver, et al., e's., McGraw–Hill, New York, NY, p. 2409–2437 (1990).

Demple and Harrison, "Repair of Oxidative Damage to DNA," *Annu. Rev. Biochem.*, 63:915–48 (1994).

Devchand, P.R., et al., "Uracil–DNA glycosylase as a probe for protein–DNA interactions," *Nucleic Acids Research*, 21:3437–3443 (1993).

Dianov, G. et al., "Preferential recognition of I–T base–pairs in the initiation of excision–repair by hypoxanthine–DNA glycosylase," *Nucleic Acids Research*, 19:3829–3833 (1991).

Duncan, "DNA Glycosylases," in *The Enzymes*, Boyer ed., p. 565–586 (1981).

Fahy, et al., "Self–sustained Sequence Replication (3SR): An Isothermal Transcription–based Amplification System Alternative to PCR," *PCR Meth. Applic.*, 1:25–33 (1991).

Floyd, R.A., et al., "Methylene Blue plus Light Mediates 8–Hydroxyguanine Formation in DNA," *Archives of Biohemistry and Biophysics*, 273:106–111 (1989).

Friedmann, T., et al., "Base–specific reactions useful for DNA sequencing: methylene blue–sensitized photooxidation of guanine and osmium tetraoxide modification of thymine," *Nucleic Acids Research*, 5:615–622 (1978).

Karran and Lindahl, "Enzymatic Excision of Free Hypoxanthine from Polydeoxynucleotides and DNA Containing Deoxyinosine Monophosphate Residues," *J. Biol. Chem.* 253(17):5877–5879 (1978).

Karran and Lindahl, "Hypoxanthine in Deoxyribonucleic Acid: Generation by Heat–Induced Hydrolysis of Adenine Residues and Release in Free Form by a Deoxyribonucleic Acid Glcosylase from Calf Thymus," *Biochemistry* 19:6005–6011 (1980).

Kwoh, et al., "Transcription–based amplification system and Detection of Amplified Human Immunodeficiency Virus Type 1 with a Bead–based Sandwich Hybridization Format," *Proc. Natl. Acad. Sci. USA* 86:1173–1177 (1989).

(List continued on next page.)

*Primary Examiner*—Jeffrey Fredman
*Attorney, Agent, or Firm*—Quarles & Brady

[57] ABSTRACT

A method of analyzing a DNA molecule is disclosed. In one embodiment the method comprises the steps of exposing a DNA molecule to an effective amount of a chemical modification reagent wherein the reagent converts guanine to 8-hydroxyguanine. The oxidized product is then exposed to a DNA glycosylase enzyme and the DNA molecule is cleaved at the site of the 8-hydroxyguanine. The fragments are then resolved by electrophoresis and the position of guanine residues within the DNA molecule is determined. In a preferred embodiment of the present invention, the modification reagent is a thiazine dye and the enzyme is FPG protein.

18 Claims, No Drawings

OTHER PUBLICATIONS

Lindahl, "An N–Glycosidase from *Escherichia Coli* that Releases Free Uracil from DNA Containing Deaminated Cytosine Resideus," *Pro. Natl. Acad. Sci. USA* 71(9):3649–3653 (1974).

Lindahl, "DNA Glycosylases, Endonucleases for Apurinic/Apyrimidinic Sites, and Base Excision–Repair," *Prog. Nucl. Acid Res. Mol. Biol.* 22:135–192 (1979).

Maxam and Gilbert, "A New Method for Sequencing DNA," *Proc. Natl. Acad. Sci. USA* 74(2):560–564 (1977).

Merajver, et al., "Somatic Mutations in the BRCA1 Gene in Sporadic Ovarian Tumours," *Nature Genetics* 9:439–443 (1995).

Myers and Gelfand, "Reverse Transcription and DNA Amplification by a *Thermus thermophilus* DNA Polymerase," *Biochemistry* 30(31):7661–7666 (1991).

Negri, R., et al., "A Single–Reaction Method for DNA Sequence Determination," *Analytical Biochemistry*, 197:389–395 (1991).

Negri, R., et al., "Chemical method for DNA sequence determination from the 5'–extremity on PCR applied fragments," *Nucleic Acids Research*, 22:111–112 (1994).

Negri, R., et al., "One–Step, One–Lane Chemical DNA Sequencing by N–Methylformamide in the Presence of Metal Ions," *Bio Techniques*, 21:910–917 (1996).

Nisson, et al., "Rapid and Efficient Cloning of Alu–PCR Products Using Uracil DNA Glycosylase," *PCR Meth. Applic.* 1:120–123 (1991).

Qu, W., et al., "PCT Detection of Human Papillomavirus: Comparison Between MY09/MY11 and GP5+/GP6+ Primer Systems," *Journal of Clinical Microbiology*, 35:1304–1310 (1997).

Pu, W.T., et al., "Uracil interference, a rapid and general method for defining protein–DNA interactions involving the 5–methyl group of thymines: The GCN4–DNA complex," *Nucl. Acids Res.* 20(4):771–775 (1992).

Rodriguez, H., et al., "Mapping of Copper/Hydrogen Peroxide–induced DNA Damage at Nucleotide Resolution in Human Genomic DNA by Ligation–mediated Polymerase Chain Reaction," *The Journal of Biological Chemistry*, 270:17633–17640 (1995).

Sanger, et al., "DNA Sequencing with Chain–terminating Inhibiitors," *Proc. Natl. Acad. Sci. USA* 74(12):5463–5467 (1977).

Saparbaev, M., et al., "Excision of hypoxanthine from DNA containing dIMP residues by the *Escherichia coli*, yeast, rat and human alkylpurine DNA glycosylases," *Proc. Natl. Acad. Sci. USA*, 91:5873–5877 (1994).

Stahl and Chamberlin, "Groups on the Outside of the DNA Helix Affect Promoter Utilization by T7 RNA Polymerase," *RNA Polymerase*, Losich and Chamberlin ed's., Cold Spring Harbor Press, Cold Spring Harbor, NY, p. 429–440 (1976).

Vaughn, P. and McCarthy, T.V., "A novel process for mutation detection using uracil DNA–glycosylase," *Nucleic Aids Research*, 26:810–815 (1998).

Yap and McGee, "Detection of Mutations by PCR,"in *PCR Technology*, Griffin and Griffin, ed's., CRC Press, Boca Raton, FL, p. 107–120 (1994).

Boiteux et al, "Substate specificty of *Escherichia coli* Fpg protein (Formamidopyrimidine–DNA glycosylase): Excision of purine lesions in DNA produced by ionizing radiation of photosensitization", Biochemistry 31:106–110, 1992.

Bej et al, "Amplification of nuleic acids by polymerase chain reaction (PCR) and other methods and their applications", Crit. Rev. Biochem. Mol. Biol. 26(3/4):301–334, 1991.

Stratagene Catalog, p. 39, 1988.

M.H. Chung, *et al.*, "An endonuclease activity of *Escherichia coli* that specifically removes 8–hydroxyguanine residues from DNA, "*Mutation Research*, 254:1–12 (1991).

T. Friedmann, *et al.*, "Base–specific reactions useful for DNA sequencing: methylene blue–sensitized photooxidation of guanine and osmium tetraoxide modification of thymine,"*Nucleic Acids Research*, 5(2): 615–622 (1978).

G. Hawkins and L.M. Hoffman, "Base excision sequence scanning, A new method for rapid sequences scanning and mutation detection,"*Nature Biotechnology* 15:803–804 (1997).

J. Tchou, *et al.*, "8–Oxoguanine (8–hydroxyguanine) DNA glycosylase and its substrate specificity," *Procedure National Academy of Science USA*, 88:4690–4694 (1991).

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 29 base pairs
      (B) TYPE: nucleic acid
      (C) STRANDEDNESS: single
      (D) TOPOLOGY: linear (ii) MOLECULE TYPE: Oligonucleotide (xi) SEQUENCE DESCRIPTION: SEQ ID NO:1:

CGGGATCCGT TTAAGGGCAC CAATAACTG                                       29

(2) INFORMATION FOR SEQ ID NO:2:

(i) SEQUENCE CHARACTERISTICS:
      (A) LENGTH: 30 base pairs
      (B) TYPE: nucleic acid
      (C) STRANDEDNESS: single
      (D) TOPOLOGY: linear (ii) MOLECULE TYPE: Oligonucleotide (xi) SEQUENCE DESCRIPTION: SEQ ID NO:2:

CGGGATCCAC GTAAGAGGTT CCAACTTTCA                                      30

(2) INFORMATION FOR SEQ ID NO:3:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (ii) MOLECULE TYPE: Oligonucleotide (xi) SEQUENCE DESCRIPTION: SEQ ID NO:3:

ACGTCTAAGA AACCATTATT ATCATGA                                         27

(2) INFORMATION FOR SEQ ID NO:4:

(i) SEQUENCE CHARACTERISTICS:
      (A) LENGTH: 20 base pairs
      (B) TYPE: nucleic acid
      (C) STRANDEDNESS: single
      (D) TOPOLOGY: linear (ii) MOLECULE TYPE: Oligonucleotide (xi) SEQUENCE DESCRIPTION: SEQ ID NO:4:

TTCGCCACCT CTGACTTGAG                                                    20

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:5:

GCMCAGGGWC ATAAYAATGG                                                    20

(2) INFORMATION FOR SEQ ID NO:6:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:6:

CGTCCMARRG GAWACTGATC                                                    20

(2) INFORMATION FOR SEQ ID NO:7:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:7:

CTGTGAGGAA CTACTGTCTT C                                                  21

(2) INFORMATION FOR SEQ ID NO:8:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:8:

GGTGCACGGT CTACGAGACC T                                                  21

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:9:

```
CAGAAAGCGT CTAGCCATGG CGTT                                                      24

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:10:

CCCTATCAGG CAGTACCACA A                                                         21

(2) INFORMATION FOR SEQ ID NO:11:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:11:

AGAGTTTGAT CCTGGCCTCA G                                                         21

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: Oligonucleotide (xi) SEQUENCE DESCRIPTION: SEQ ID NO:12:

CTGCTGCCTC CCGTAGGAGT                                                           20
```

METHOD OF IDENTIFYING NUCLEIC ACID MOLECULES

CROSS-REFERENCE TO RELATED APPLICATION

Not applicable.

STATEMENT REGARDING FEDERALLY SPONSORED RESEARCH OR DEVELOPMENT

Not applicable.

BACKGROUND OF THE INVENTION

Methods of Characterizing Nucleic Acid Molecules

A variety of methods for characterizing DNA molecules are known in the art. For example, one can characterize DNA molecules by size based on their electrophoretic migration through an agarose or polyacrylamide gel. Another way to characterize DNA molecules is to treat each DNA molecule with one or more restriction endonucleases and then to determine the sizes of the various DNA fragments resulting from this treatment by agarose gel electrophoresis. Additionally, changes such as those caused by mutations in DNA may result in a loss or gain of restriction site—a so-called "restriction fragment length polymorphism" (RFLP). An example of a diagnostically significant RFLP is a single base mutation in the beta-hemoglobin gene, the change from A to T, which eliminates a DdeI restriction site and results in sickle cell anemia.

One of the most informative ways to characterize a DNA molecule is to determine its nucleotide sequence. One method for sequencing DNA (Maxam and Gilbert, 1977) is accomplished by treating each of four aliquots of one strand of a 5'- or 3'-end labelled DNA molecule to be sequenced with one of four different chemical reagents. The most commonly used method for sequencing DNA at this time (Sanger, et al., 1977) uses a DNA polymerase to produce differently sized fragments depending on the positions (i.e., sequence) of the four canonical bases (A=Adenine; C=Cytidine; G=Guanine; T=Thymine) within the DNA to be sequenced. Cycle Sequencing is a variation of Sanger sequencing that achieves a linear amplification of the sequencing signal by using a thermostable DNA polymerase and repeating chain terminating DNA synthesis during each of multiple rounds of denaturation of a template DNA (e.g., at 95° C.), annealing of a single primer oligonucleotide (e.g., at 55° C.), and extension of the primer (e.g., at 70° C.).

In order to characterize a nucleic acid by sequencing, the nucleic acid must be isolated in sufficient quantity to be used for the particular method. Although it may be possible to obtain sufficient quantities of a nucleic acid for sequencing by first cloning it into a plasmid or other vector, this procedure is time-consuming and is often not practical for routine analysis of samples for clinical diagnostics or other purposes. When the amount of nucleic acid in a sample is less than optimal for a given method, it may be advantageous to use one of several methods which have been developed for amplifying parts of nucleic acid molecules. The polymerase chain reaction (PCR) as described in U.S. Pat. Nos. 4,683,195 and 4,683,202, incorporated herein by reference, nucleic acid sequence-based amplification (NASBA) as described in U.S. Pat. No. 5,234,809 incorporated herein by reference, self-sustained sequence replication (3SR), transcription-mediated amplification (TMA) as described in U.S. Pat. No. 5,399,491 incorporated herein by reference, and strand displacement amplification (SDA) are examples of some of the methods which have been developed for amplifying nucleic acid molecules in vitro. RNA may also be amplified using one of several protocols for RT-PCR as described in U.S. Pat. No. 5,310,652 incorporated herein by reference, such as, for example, by carrying out the reaction using a thermostable DNA polymerase which also has reverse transcriptase activity (Myers and Gelfand, 1991).

Although PCR, NASBA and other of nucleic acid amplification methods are useful for obtaining greater quantities of a nucleic acid for additional characterization, such amplification methods pose difficulties when used in conjunction with sequencing. In general, the amplified nucleic acid molecules must be purified away from primers, nucleotides, incomplete amplification products and other impurities prior to being used for sequencing. Otherwise, for example, the PCR primers may compete with labelled sequencing primers and the PCR nucleotides may compete with the sequencing nucleotide mixes that are used for Sanger dideoxy sequencing. Also, Sanger sequencing normally cannot be done at the same time as PCR or another amplification method, at least not efficiently, because the dideoxynucleotides used for sequencing will result in termination of the DNA amplification reactions as well as the sequencing reactions.

One group has developed a method that attempts to decrease the number of steps required for sequencing nucleic acids (Shaw and Porter, PCT WO 95/06752). According to this method, 5'-alpha-borano-deoxynucleoside triphosphates, which were found to be resistant to exonuclease III (exo III) digestion, were incorporated into DNA during in vitro DNA synthesis in lieu of a portion of one of the canonical nucleotides (DATP, dCTP, dGTP, dTTP) in one of four primer extension reactions. Treatment with exo III will digest the synthesized DNA up to the point of alpha-borano deoxynucleoside incorporation. After digestion with exo III and resolution of the labelled fragments on a polyacrylamide gel, the sequence of the nucleic acid can be determined.

An advantage of the alpha-borano/exo III method is that it can be integrated into PCR amplification. However, there are also disadvantages. A key disadvantage is a lower degree of accuracy of the sequence data compared to Maxam-Gilbert or Sanger sequencing because the alpha-borano/exo III method gives both extra bands and missing bands on sequencing gels. Another serious disadvantage of the alpha-borano/exo III method is related to the substrate requirements of exo III. Because exo III digests only double-stranded DNA, beginning at the 3'-end of each strand, the sequence can only be determined for the 3'-half of each strand of a PCR product, so it is not possible to obtain the sequence near to the primer. Also, because exo III digestion yields only fragments that are between 50% and 100% of the length of the full-size PCR product, the size range of the DNA which can be sequenced by the method is somewhat limited. For example, if a PCR product of 1000 base pairs in length is sequenced according to the alpha-borano/exo III method, the fragments to be electrophoresed would be approximately 500–1000 nucleotides long. Fragments of such a length are more difficult to resolve in DNA sequencing gels.

The technique of single-strand conformation polymorphism (SSCP) is another technique that compares the electrophoresed fragment mobility of PCR products. SSCP and the closely related hetroduplex analysis methods have come into use for screening for single-base mutations (Orita, et al., 1989; Keen, et al., 1991). In these methods, the mobility of PCR-amplified mutated DNA is compared with the mobility of DNA amplified from normal or wild-type DNA by direct electrophoresis of samples in adjacent lanes of native polyacrylamide or other types of matrix gels. Single-base mutations often alter the secondary structure of the molecule sufficiently to caused slight mobility differences between the normal and mutant PCR products after prolonged electrophoresis.

Unfortunately, SSCP has several major drawbacks. The most important is that not all mutations result in detectable shifts in mobility. For instance, it has been shown that of 20 mutations detected by direct sequencing, only 35% were detected by SSCP (Sarkar, et al., 1992). Other studies have reported higher detection efficiencies, but it is well known in the art that SSCP has a major problem in missing point mutations. The chances of detecting mobility differences can be increased by running parallel gels under different conditions, for example at 4° C. and 30° C., with and without 5% glycerol, (Hayashi, 1991), but this significantly increases the cost and labor associated with analysis. Since mobility differences are generally quite small, analysis of genes in the heterozygous state is compromised. Another drawback of SSCP and related techniques is that they provide no information on the position of the mutation within the DNA fragment being analyzed. And finally, there seems to be an upper size limit for analysis by SSCP of approximately 300 bases and increased fragment length has been associated with decreased efficiency of mutation detection (Hayashi, 1991).

The technique of restriction endonuclease fingerprinting (REF) (Liu and Sommer, 1995) combines two mutation detection methods. The change of electrophoretic mobility under SSCP conditions of a DNA fragment containing a mutation is combined with the possible alteration of a restriction endonuclease site. The method requires a labeling step following the restriction endonuclease cleavage and suffers the same drawback of SSCP, namely the need for extensive optimization of gel conditions. Another modification of SSCP, dideoxy fingerprinting (ddF) (Sarkar et al., 1992), requires transcription of a PCR product into an RNA molecule, a DNA sequencing reaction with a single dideoxy terminator, and a non-denaturing, high resolution gel. The ddF method is limited in the size of DNA fragments analyzed and the localization of mutants is only within ten bases of the mutation locus (Blaszyk, et al., 1995).

U.S. Ser. No. 08/534,799 discloses a method of characterizing a nucleic acid in which non-canonical deoxynucleotide triphosphates are incorporated during the process of nucleic acid amplification.

FPG Protein

DNA repair is a fundamental biological process that ensures the stability and integrity of the genome. DNA repair enzymes are often classified according to the manner in which they promote removal of DNA damage. DNA glycosylases, known generally as base excision repair enzymes, are a specific class of DNA repair enzymes that catalyze the hydrolysis of the N-glycosidic bonds linking particular types of chemically modified bases or incorrectly inserted bases to the deoxyribose-phosphodiester backbone.

One of the best-known DNA N-glycosylases, uracil N-glycosylase (UNG), is used in vitro to prevent accidental carryover of PCR products into other reactions (see for example U.S. Pat. No. 5,035,996). In such a scheme, the PCR reaction contains dUTP that is incorporated in place of dTTP into the PCR product. The PCR product may then be degraded by the action of UNG and heat, which results in breakage of the DNA at the dU residues. Another method using UNG is the use of dU-containing PCR primers for cloning the product (Watson and Bennett, 1997). Following PCR with the dU-containing primers, the product is digested with UNG, which in effect cleaves off the 5'-ends, or a part of the ends of the PCR product. The vector contains complementary 5' overhanging termini which may be used to anneal and ligate the PCR product to the vector. DNA N-glycosylases have also been used to measure the amount of base damage to DNA in organisms subjected to different conditions. The cellular DNA is extracted, cleaved with a glycosylase, and the bases released by the glycosylase are analyzed or the presence of abasic sites in the DNA is determined.

UNG has also been used to "footprint" the binding sites of proteins on DNA molecules (Devchand, et al., 1993). dUTP is incorporated randomly into an end-labeled DNA, which is reacted with a protein or protein mixture. The specific binding of proteins is detected by the protection of a region of the DNA from UNG degradation.

UNG has also been used to detect mutations by a method involving incorporation of only dUTP in place of TTP (Vaughn and McCarthy, 1998; Vaughn and McCarthy, International application PCT/IE95/00067, 1997).

Formamidopyrimidine DNA N-glycosylase (FPG protein) is a base excision repair enzyme that recognizes chemically modified bases and catalyzes the cleavage of the N-glycosyl linkage between a modified base and the deoxyribose-phosphodiester backbone in DNA. In addition, FPG protein also possesses an apyrimidinic/apurinic (AP) lyase activity.

The N-glycosylase activity of FPG protein releases damaged bases from DNA, generating an AP site. The AP-lyase activity of the enzyme catalyzes $\beta$, $\delta$-elimination reactions, leaving a single nucleotide gap in the DNA (Bailly, et al., 1989a). The resulting products arising from a damaged base or an AP site include a monomeric five-carbon fragment derived from deoxyribose (Bhagwat and Gerlt, 1996) and a one-base gapped DNA terminated by 3' and 5' phosphates (Bailly, et al., 1989b).

FPG protein recognizes diverse but structurally related DNA base modifications including, but not limited to, 8-hydroxyguanine (also known as 7-hydro-8-oxoguanine or 8-oxoguanine, referring to the favored 6,8-diketo tautomer at physiological pH) (Tchou, et al., 1991), imidazole ring-opened derivatives of adenine or guanine, designated 4,6-diamino-5-formamidopyrimidine and 2,6-diamino-4-hydroxy-5-formamidopyrimidine, respectively, (Chetsanga, et al., (1981) and Breimer (1984)), $N_7$-methylformamidopyrimidines, 5-hydroxyuracil and 5-hydroxycytosine (Hatahet, et al., 1994).

As used herein, "FPG protein" includes and is also known in the art as 8-hydroxyguanine DNA glycosylase, which recognizes 8-hydroxyguanine residues in DNA. Indeed, both FPG protein and 8-hydroxyguanine DNA glycosylase have been shown to be identical (Chung, et al., 1991).

Photoactive Dye Mutagenesis

Methylene blue is a thiazine dye which has been used for veterinary, pharmaceutical and other biological purposes (Vennerstrom, et al., 1995; Deutsch, et al., 1997). Exposure of DNA to methylene blue plus light caused guanine-specific modifications and that subsequent piperidine treatment of the modified DNA led to chain cleavage at guanine residues (Friedmann and Brown, 1978). Using the method of DNA sequencing described by Maxam and Gilbert (Maxam and Gilbert, 1977), including piperidine treatment to induce chain cleavage, Friedmann and Brown were able to determine the nucleotide sequence in DNA.

The photosensitizer methylene blue plus visible light produces DNA base damage that is recognized and subsequently removed by FPG protein. The DNA damage from methylene blue (MB) plus light has been reported to be caused by the production of singlet oxygen (Epe, et al., 1993), and the great majority of the damage is specific for guanine residues (Floyd, et al., 1989). The most prevalent type of damaged base, 8-hydroxyguanine, is mutagenic, which leads to guanine (G) to thymine (T) transversion mutations in DNA (Cheng, et al., 1992).

Rose bengal, an anionic xanthene dye, in the presence of ultraviolet radiation induces guanine-specific modifications, similar to those types guanine-specific modifications generated by methylene blue plus light (Friedman and Brown, 1978).

Needed in the art of molecular biology and diagnostics is a method for characterizing nucleic acids that is as accurate and as specific as DNA sequencing for detection or identification of nucleic acids, but that is simpler, faster, and requires less template DNA than dideoxy sequencing reactions. The method should also be useful for relatively impure nucleic acid samples, such as amplification products, eliminating the need to purify the sample from primers, nucleotides, other enzymes, or other impurities.

BRIEF SUMMARY OF THE INVENTION

The present invention is a simple and reliable method to identify nucleic acid polymers. Because no special or non-canonical deoxynucleoside triphosphates necessarily need to be incorporated during the method, the DNA for this dG-specific cleavage method may be prepared by using a standard amplification method such as PCR, NASBA, SDA, or isothermal DNA synthesis reactions. In principal, any DNA containing a label at or near the 5' terminus label can be analyzed using the present invention. Alternatively, a DNA molecule containing invariant 3' termini can be analyzed using the present invention if DNA is labelled at or near the 3'-end.

In one preferred embodiment of the present invention, a DNA molecule is synthesized in the presence of a nucleic acid template. The in vitro synthesized DNA is exposed to a chemical modification reagent under conditions that structurally modify a portion of the guanine bases. The DNA is then treated with an enzyme that recognizes and excises the modified bases from the DNA chains.

In one embodiment, the preferred enzyme is formamidopyrimidine DNA N-glycosylase (FPG protein), alternatively known as 8-hydroxyguanine DNA glycosylase. FPG protein is also an apyrimidinic/apurinic endonuclease that cleaves the phosphodiester bonds adjacent to the removed base.

In another preferred embodiment, the apyrimidinic/apurinic endonuclease is a second enzyme, preferably endonuclease IV, which may be used to "polish" the termini of the broken DNA chains by removing the 3' phosphate groups left by the FPG protein.

The resulting DNA fragments are a nested set of molecules of different lengths, each size class corresponding to the site where a modified guanine base was found in the original molecule. Size resolution of the set of cleaved DNA fragments by gel electrophoresis reveals the position of the modified bases. Therefore, the positions of that base in the DNA strand can be determined.

In still another embodiment, the invention is a kit for performing the method described above. The kit comprises a thiazine dye such as methylene blue, a glycosylase, and an enzyme cleavage buffer. In another embodiment, the kit also contains an AP endonuclease. In still additional embodiments, the kit also contains one or more of the following: (a) primers for PCR, (b) a thermostable polymerase, (c) deoxyribonucleoside triphosphates, or (d) other reagents as necessary for performing other reactions.

It is an object of the present invention to determine the presence or location of guanine residues in a DNA molecule.

It is another object of the present invention to be able to identify a DNA molecule in terms of its guanine residue sequence.

It is a feature of the present invention that the method is useful for relatively impure nucleic acid samples, such as amplification products, and eliminates the need to purify the sample from primers, nucleotides, other enzymes or impurities.

Synthesis of DNA for the dg-specific cleavage by PCR or by another amplification method using at least one labelled primer enables the present invention to require less DNA than previous DNA sequencing methods.

Other objects, advantages and features of the present invention will become apparent after one of skill in the art studies the specification and claims presented herewith.

DETAILED DESCRIPTION OF THE INVENTION

1. In General

In one embodiment, the present invention is a method for identifying a nucleic acid. In a preferred embodiment, the present invention provides a method for identifying the positions of the deoxyguanosine nucleotide components of nucleic acid molecules. The method includes the steps of converting a portion of the guanines to an oxidized form, excising the oxidized guanine bases, breaking the phosphodiester backbone of the DNA at the abasic sites, and analyzing the resulting DNA fragments.

In one preferred embodiment, the production of 8-hydroxyguanine bases is catalyzed by the presence of methylene blue and light.

In a preferred form of the present invention, the DNA for the dG-specific cleavage analysis is prepared using a DNA amplification method such as PCR, NASBA, TMA or SDA.

Preferred methods for labeling the 5'-end of DNA for the methods herein described include, but are not limited to, standard methods of polynucleotide kinase labeling of the 5' termini with $\gamma$-$^{32}$P ATP and attachment of a fluorescent moiety, such as a fluorescein- or rhodamine-based dye, or attachment of biotin, to the 5' terminus of a DNA molecule.

If, according to the present invention, the DNA for the dG-specific cleavage is synthesized by PCR or another method, a radioactive or non-radioactive label may be incorporated into an oligonucleotide primer used for the amplification by standard methods known in the art. Custom oligonucleotide primers, including those labelled with a variety of non-radioactive dyes or other moieties, may be obtained from commercial sources. If both strands of the DNA to be characterized using the invention are labelled, each strand must be labelled with a different label that is distinguishable from the other by the detection system used. For example, DNA may be characterized using the invention by using dye labels that are available for automated DNA sequencing, and then analyzing the data on an automated DNA sequencer, such as the Applied Biosystems Model 377 or Model 310, or on a scanner, such as the Hitachi FM-Bio II, or another suitable instrument. Interpretation of the data is facilitated by using software, such as the GeneScan software for Applied Biosystems instruments, or other suitable software. Multiple DNA samples and/or multiple reactions may be analyzed in the same well of a sequencing gel or during the same run in a capillary if different distinguishable dyes are used in each case.

Another method for labeling the 5'- or 3'-ends of DNA for the methods described herein is to ligate a labeled oligonucleotide specifically to only one end of the DNA to be analyzed using methods known in the art.

In another preferred embodiment, the DNA molecules containing dU which are produced according to U.S. Ser. No. 08/534,799, which is herein incorporated by reference, may be additionally analyzed for the positions of dG residues. U.S. Ser. No. 08/534,799 discloses a method of characterizing a nucleic acid in which non-canonical deoxynucleotide triphosphates are incorporated during the process of nucleic acid amplification. That is, the same PCR products which are being analyzed for dU, and by inference for dT, may be analyzed for dG by the present invention. By performing both dU- and dG-specific reactions on both strands of the DNA, one may determine the presence of any mutation involving any of the four canonical bases.

We envision that software to analyze data for both DNA strands from both dU-specific reactions and dG-specific reactions can be developed to obtain the complete sequence of the DNA, especially in a diagnostic-type situation in which the same gene or DNA region is being examined for different samples. The software would use the data for the second DNA strand in order to call the complementary bases on the first strand and then align that sequence information in the correct direction and in the correct position relative to the data obtained from each dU-specific and dG-specific reaction for the first strand. Characteristic sequence patterns within the DNA will facilitate the sequence alignment.

Both dU-specific reactions and dG-specific reactions, as well as both DNA strands in each case, may be analyzed in the same well of a sequencing gel or during the same run in a capillary if different distinguishable dyes or other non-radioactive moieties are used to label each reaction and/or each DNA strand, respectively.

Another embodiment of the present invention is a kit for performing the method described above. In one embodiment the kit contains a means for converting a portion of the guanines in a target DNA sample to an oxidized form and an enzyme capable of excising the oxidized bases and an enzyme capable of breaking the phosphodiester backbone of the DNA at the abasic sites. Preferably, the oxidation means is a thiazine dye, such a methylene blue or Taylor's blue, and the enzyme is FPG protein, which has both enzymatic activities.

2. Conversion of Guanine to Oxidized Form

In the present invention, the action of chemical modification reagents and/or radiation after or during nucleic acid amplification is required to modify a portion of the guanine residues. A suitable modification reagent is any reagent capable of converting or modifying guanine to 8-hydroxyguanine. As described below, preferable reagents include dyes, such as thiazine and xanthine dyes. The modification of bases may be performed on DNA chains containing only canonical bases or a mixture of canonical and non-canonical bases. The bases so modified by the reagents and/or radiation are then excised by an enzyme specific for the reagent plus radiation-modified base. The DNA chain will then be cleaved at the abasic sites corresponding to the positions of each modified base.

If only a portion of all DNA molecules contains a modified base at any given position in the DNA molecule, the separation of the resulting DNA fragments yields patterns of nucleic acid molecules which end at the positions where the modified bases were removed. If the modification is specific for one type of base and if the enzyme used to cleave the modified DNA is specific for only one modified base, the cleavage positions correspond to the positions of that modified base within the nucleic acid being characterized.

In the preferred embodiment of the invention, the modified DNA base is guanine. It is known in the art that one of the major oxidative products in DNA is 8-hydroxyguanine, whose presence in DNA is highly mutagenic (Cheng, et al., 1992). A preferred embodiment of the present invention requires the conversion of guanine to 8-hydroxyguanine by an oxidative process. The conversion to 8-hydroxyguanine proceeds after the amplification of the nucleic acid, if used, avoiding the possible mutagenic effects of the modified base if the modified base were incorporated during the amplification.

In the preferred embodiment of the invention, a thiazine dye, such as methylene blue, and visible light mediate the oxidative process to form 8-hydroxyguanine bases in DNA (Floyd, et al., 1989; see also U.S. Pat. No. 4,950,665, both incorporated herein by reference).

The number of guanine bases converted to 8-hydroxyguanine can be controlled through manipulation of the concentration of methylene blue, light intensity and length of exposure, pH, and buffer strength. Moreover, the number of guanines oxidized in a single DNA molecule may vary and is dependent on the overall dG content of the DNA fragment. Ideally, a single dG is oxidized per strand of DNA; however, more than one dG may be modified in a single DNA target without compromising the subsequent excision of oxidized guanines and resolving the DNA fragments by electrophoresis.

When the DNA target is labelled at or near the 5'-end or 3'-end and when the target DNA has at least one oxidized guanine, all oxidized guanines will be excised, but only the oxidized dG nearest the end label (either 5' or 3') will result in DNA sequence data.

In preferred embodiments at least one guanine base is modified. Typically, between about 0.05% to about 1.5%, preferably between about 0.1% to about 1%, of guanine bases in the total population of DNA molecules are modified. By "about" we mean ±20%.

Preferably, one exposes the DNA molecules to methylene blue and visible light in the manner described below in the Examples. However, other variations of this method are possible.

Rose bengal, an anionic xanthene dye, in the presence of ultraviolet radiation induces guanine-specific modifications, similar to those types guanine-specific modifications generated by methylene blue plus light (Friedman and Brown, 1978). Therefore, one could also use the rose bengal system for modification.

3. Excising the Oxidized Bases and Cleaving the DNA Molecule

The method of the present invention then requires that the modified guanine bases be excised using a DNA glycosylase enzyme and that the DNA be cleaved at this excision point.

The present invention is an improvement over the methods of Friedman and Brown (1978) in that no hot (90° C.) piperidine treatment is needed for cleavage of the methylene blue/light-reacted DNA. Instead, a mild enzymatic treatment may be used to cleave the modified base from the DNA and to break the phosphodiester bonds at the resulting abasic sites, which also eliminates the need to remove piperidine from the reaction before gel electrophoresis. Unlike previous methods that used piperidine treatment for DNA chain cleavage, FPG protein is reacted at 37° C. for 15–30 minutes with the DNA.

In one aspect of the present invention, the mild enzymatic treatment comprises using a DNA glycosylase enzyme that recognizes and excises the modified bases from the DNA chains, thereby generating an apurinic/apyrimidinic (AP) site. As used herein, a DNA glycosylase enzyme of the present invention is any enzyme capable of cleaving the N-glycosidic linkage of 8-hydroxyguanine in DNA. In another aspect of the present invention, the mild enzymatic treatment comprises using an AP lyase to break the phosphodiester bond at the 8-hydroxyguanine site, thereby forming DNA fragments. The activities required for both aspects of the present invention may employ a single enzyme or more than one enzyme. Preferably, the DNA glycosylase enzyme is formamidopyrimidine DNA N-glycosylase (FPG protein), since both N-glycosylase and AP lyase activities reside in the same molecule; that it, only a single enzyme is required.

If the DNA glycosylase enzyme does not possess AP lyase activity to break the phosphodiester bond, then a second enzyme possessing either an AP lyase or an AP endonuclease activity must be added to the reaction.

Preferably, an AP endonuclease is added to the reaction to cleave the 3'-phosphate groups resulting from the AP lyase activity of a DNA glycosylase enzyme. As used herein, an AP endonuclease for the present invention is any enzyme capable of cleaving the 3'-phosphate groups from the products of DNA phosphodiester bond breakage. In one preferred embodiment of the invention, the AP endonuclease is endonuclease IV.

4. Analyzing the Cleavage Product

After treatment with glycosylase and lyase, the reaction products are typically electrophoresed as described below in an 8% polyacrylamide/7 M urea denaturing gel. The products may also be analyzed by other methods known in the art for separating nucleic acid molecules based on size, such as but not limited to, capillary electrophoresis.

One then examines the ladder of bands corresponding to the G reaction and is able to determine the pattern of guanine placement within the nucleotide strand. From this information, one may identify the strand, as described below in Example 3 for a portion of the human papilloma virus or Example 4 for the hepatitis C virus.

EXAMPLES

Example 1

A polymerase chain reaction (PCR) was performed to amplify the chloramphenicol acetyl transferase (CAT) gene of plasmid pT7Blue/CAT5, which contained the CAT gene from plasmid pACYC184. The primers used to amplify the CAT gene were CAT.5BAM, 5'-CGGGATCCGTTTAAGGGCACCAATAACTG-3' (SEQ ID NO:1) and CAT.3BAM, 5'-CGGGATCCACGTAAGAGGTTCCAACTTTCA-3' (SEQ ID NO:2). The CAT.5BAM primer was $^{32}$P-end-labelled by standard methods (Maxam and Gilbert, 1977).

One nanogram of plasmid pT7Blue/CAT5 was added to PCR reactions of 50 microliters, containing 10 mM Tris-HCl pH 8.3, 50 mM potassium chloride, 2.5 mM magnesium chloride, 0.2 mM each dGTP, dATP, dTTP, and dCTP, 5 pmole of each primer, and 5 units of Tfl DNA polymerase (Epicentre Technologies, Madison, Wis.). The reactions were subjected in an MJ Research PTC-2000 thermocycler with the following cycling regimen: 95° C. for 3 minutes, then four repetitions of 94° C. for 30 seconds, 49° C. for 10 seconds with a decrease of 1.5° C. per repetition, and 68° C. for one minute, then thirty repetitions of 94° C. for 10 seconds and 70° C. for one minute, then 72° C. for 2 minutes, then 4° C. indefinitely.

Following amplification the samples were treated with 5 or 15 minutes of visible light at about 20,000 lux from a halogen lamp in the presence of 20 micrograms per milliliter (approximately 62 micromolar) of methylene blue. Thirty-six ng of FPG protein (Epicentre Technologies, Madison, Wis.) or an equal volume of storage buffer, and 1 μl of buffer containing 1.0 M Tris-HCl, pH 9.0, 0.4 M ammonium sulfate and 100 mM EDTA were added to PCR product and each mixture was reacted for 30 minutes at 37° C. Three μl of stop/loading solution were added to the reactions and they were electrophoresed in an 8% polyacrylamide/7M urea denaturing gel.

For both 5 and 15 minute photoperiods, a ladder of bands corresponding to the "G" reaction from the dideoxynucleotide (Sanger, et al., 1977) sequencing of the same plasmid was found. The glycosylase-derived bands migrated approximately one nucleotide space faster than the corresponding Sanger sequence "G" ladder bands.

Example 2

A PCR containing a $^{32}$P-end-labelled primer 5'-ACGTCTAAGAAACCATTATTATCATGA-3', (SEQ ID NO:3), an unlabelled primer 5'-TTCGCCACCTCTGACTTGAG-3', (SEQ ID NO:4), pUC19 plasmid (10 ng), buffer and nucleotide mixture supplied in the BESS T-Scan™ kit (Epicentre Technologies, Madison, Wis.), and 0.2 units of Tfl polymerase (Epicentre Technologies, Madison, Wis.) was subjected to thermal cycling in an MJ Scientific Minicycler. Cycling conditions were as follows: 94° C. 4 minutes, then 34 cycles of 94° C. for 1 minute, 58° C. for 1 minute and 73° C. for 1 minute and 20 seconds, followed by 73° C. for 4 minutes.

The approximately 1000 base pair PCR product was then treated with a variety of conditions (Table 1) to ascertain the effects of several variables.

TABLE 1

| SAMPLE | METHYLENE BLUE | ENDO-NUCLEASE IV | FPG PROTEIN | HIGH INTENSITY LIGHT EXPOSURE |
| --- | --- | --- | --- | --- |
| 1 | + | + | + | 5 minutes |
| 2 | + | + | + | 15 minutes |
| 3 | + | + | -- | 15 minutes |
| 4 | + | -- | + | 15 minutes |
| 5 | + | -- | -- | 15 minutes |
| 6 | + | + | + | room light only |
| 7 | -- | + | + | 15 minutes |

The reactions were stopped with a formamide-containing loading buffer and electrophoresed in a denaturing polyacrylamide gel as in Example 1. The results corresponding to the samples in Table 1 are summarized in Table 2:

TABLE 2

| SAMPLE | RESULTS |
| --- | --- |
| 1 | dG-specific bands to end of readable portion of gel |
| 2 | dG-specific bands to end of readable portion of gel |
| 3 | some smearing, but no dG banding |
| 4 | similar to sample 1, but bands migrate more slowly |
| 5 | some smearing, but no dG banding |
| 6 | similar to sample 1 |
| 7 | only PCR product band |

The results indicate that: (1) dG-specific reactions with methylene blue plus light may be performed on DNA containing dU (for example, DNA prepared for analysis with the BESS T-Scan™ kit of Epicentre Technologies, Madison, Wis.); (2) the reaction is dependent upon the presence of methylene blue; (3) the reactions may be performed with only normal ambient lighting; (4) the addition of endonuclease IV to the enzyme FPG protein during the glycosylase reaction produces sharper DNA bands which migrate more closely to the corresponding dideoxy (Sanger) sequencing ladder pattern than samples with only FPG protein.

Example 3

PCR was used to amplify the L1 region of human papilloma virus (HPV). The L1 genomic region, encoding the major capsid protein of the virus, is hypervariable in different HPV strains. Two clones encoding HPV types 16 and 18, potentially oncogenic strains of the DNA virus, known to differ in their DNA sequences were the targets of amplification. Ten nanograms of plasmid clones of HPV (provided by Dr. Paul Lambert, University of Wisconsin-Madison) were amplified in a 25 μl reaction containing 10 mM Tris-HCl, pH 8.3, 50 mM KCL, 3.5 mM magnesium chloride, 10 pmoles of primer MY11, 5'-GCMCAGGGWCATAAYAATGG (SEQ ID NO:5), where M=A or C, W=A or T, and Y=C or T, 10 pmoles of $^{32}$P-labelled primer MY09, 5'-CGTCCMARRGGAWACTGATC (SEQ ID NO:6), where R=A or G, 1×BESS T-Scan™ dNTP mixture (Epicentre Technologies, Madison, Wis.) and 5 units of Taq DNA polymerase (Epicentre Technologies, Madison, Wis.). The mixture was processed as follows in a MJ Research Minicycler: 94° C. for 4 minutes; 35 cycles of 94° C. for 1 minute, 56° C. for 1 minute, and 73° C. for 1 minute; followed by 73° C. for 4 minutes; 4° C. for indefinite hold.

Samples of the PCR were subjected to light and cationic thiazine dyes, followed by cleavage with FPG protein and endonuclease IV. A second variety of cationic thiazine dye, Taylor's Blue (1,9-dimethylmethylene blue) was evaluated. The effects of light box illumination on the production of 8-hydroxyguanine in PCR products in the presence of either dye was also tested.

The reaction protocol in Example 1 was modified by the inclusion of Taylor's Blue at 20 micromolar concentration in some samples. Samples were treated with the dyes and with or without a 10 minute light box exposure, reacted with a combination of FPG protein and endo IV enzymes as described in Example 2, and electrophoresed in a small format denaturing polyacrylamide gel (QuickPoint™ Rapid Nucleic Acid Separation System, Novel Experimental Technology, San Diego, Calif.).

The results showed the clearest bands were obtained with light box exposure and methylene blue treatment. The banding pattern of DNA fragments with dG residues in HPV type 16 was distinctly different from that of HPV type 18. We conclude that (a) the two strains of HPV are easily identified and distinguished using the samples which were exposed to the light box and contained methylene blue or Taylor's Blue (b) Methylene Blue is more effective than Taylor's Blue under the conditions tested, and (c) light box exposure was essential to obtain detectable levels of dG cleavage bands in the samples under the conditions used.

Example 4 dG-specific analysis was performed on the 5'-noncoding region (5'NCR) of hepatitis C virus (HCV). Initially, RNA virion sequences were converted to cDNA, which was used as a template for the PCR. PCR primers and human serum containing HCV were kindly provided by Dr. Yury Khudyakov and Dr. Howard Fields, Hepatitis Branch, Centers of Disease Control, Atlanta, Ga. Total RNA was isolated from 50 μl of serum using the Epicentre Master Pure™ RNA Isolation Kit according to the manufacturer's protocol (Epicentre Technologies, Madison, Wis.). RT-PCR was performed using the Epicentre MasterAmp™ RT-PCR Kit. The sequences of the primers are as follows: HCVRT-F 5'-CTGTGAGGAACTACTGTCTTC-3' (SEQ ID NO:7); HCVRT-R 5'- GGTGCACGGTCTACGAGACCT-3' (SEQ ID NO:8). The primers amplify a 296 bp fragment of the 5'NCR corresponding to bases 28 to 323 of the representative HCV type 1b sequence HCVJK1G (Genbank accession number X61596).

Each 25 μl RT-PCR contained about 100–400 copies of HCV RNA template, 1×MasterAmp™ RT-PCR buffer, 3 mM MgCl$_2$, 0.5 mM MnSO$_4$, 2×MasterAmp™ PCR Enhancer (with betaine), 400 μM dNTP's, 25 pmoles of each forward and reverse primer and 1.25 U of RetroAmp™ DNA polymerase was subjected to thermal cycling in an MJ Scientific Minicycler. Cycling parameters were as follows: 60° C. for 20 minutes (RT reaction), 92° C. for 2 minutes, followed by 35 cycles of 92° C. for 1 minute, 54° C. for 1 minute and 68° C. for 1 minute, and finishing with a 4 minute incubation at 68° C. (MasterAmp™ and RetroAmp™ are products of Epicentre Technologies, Madison, Wis.).

A second PCR using an internal nested primer set was performed on the RT-PCR products. The sequences of the primers are as follows: HCVIN-F 5'-CAGAAAGCGTCTAGCCATGGCGTT-3' (SEQ ID NO:9); HCVIN-R 5'-CCCTATCAGGCAGTACCACAA-3' (SEQ ID NO:10). The primers amplify a 232 bp fragment of the 5'NCR corresponding to bases 52 to 284 of the representative HCV type 1b sequence HCVJK1G (Genbank accession number X61596). Briefly, all RT-PCR products were diluted 100-fold in TE pH 8.0 and used in PCR as follows. Each 25 μl reaction contained 1 μl of diluted RT-PCR product, 1×PCR buffer, 200 μM of BESS T-Scan™ dNTP mix, 2 mM MgCl$_2$, 2X MasterAmp™ PCR Enhancer (with betaine), 10 pmoles of $^{32}$P-labelled primer, 10 pmoles of unlabelled primer and 0.5 U of MasterAmp™ Taq polymerase (BESS T-ScanTM and MasterAmp™ products from Epicentre Technologies, Madison, Wis.) was subjected to thermal cycling in an MJ Scientific Minicycler. Cycling parameters were as follows: 94° C. for 2 minutes, followed by 30 cycles of 94° C. for 1 minute, 64° C. for 1 minute and 73° C. for 1 minute, and finishing with a 4 minute incubation at 73° C.

Five μl of each PCR was placed in a clear 0.5 ml microcentrifuge tube and 0.5 μl of the 10×BESS T-Scan™ Excision Enzyme Buffer (Epicentre Technologies, Madison, Wis.) and 0.5 μl of 200 μg/ml methylene blue (final concentration 20 μg/ml). The tubes were vortexed for 30 seconds and placed directly on the surface of a fluorescent light box (visible light) for 10 minutes. After illumination, 0.5 μl of an excision enzyme mix comprising FPG protein and endonuclease IV was added and the mixture incubated for 30 minutes at 37° C. Each reaction was stopped by adding 3 μl of stop/loading dye, and the DNA was fractionated on an 8% denaturing gel in a glycerol-tolerant buffer.

Isolates 139, 141, 142, 151, 412 and 446 all conformed to the consensus dG sequence patterns of HCV type 1a or 1b. The only slight variation in this group was isolate 446, which possessed a single base shift at base 192 due to a single base insertion in its sequence. Only two isolates had significant pattern variations: isolates 165 and 411. The dG patterns of both 165 and 411 conformed significantly to the consensus sequence of HCV type 2b. However, one sequence change at base 125 was noted between isolates 165 and 411, thus establishing each isolate as a separate subtype.

Example 5

The G specific reaction was used to analyze PCR fragments generated directly from RNA. In this example, the RNA template was 16S rRNA from *E. coli*. The primers used for the RT-PCR amplification were EB-R 5'-AGAGTTTGATCCTGGCCTCAG-3' (SEQ ID NO:11) and EB-L 5'-CTGCTGCCTCCCGTAGGAGT-3' (SEQ ID NO:12) (Brow, et al.). EB-R was radiolabelled on the 5' end using $\gamma$-$^{32}$P-ATP and T4 polynucelotide kinase (Epicentre Technologies, Madison, Wis.).

Each 50 µl reaction contained 1 ng-1 µg of total *E.coli* RNA, 400 µM of BESS T-Scan™ dNTP mix, 3.5 mM of $MgCl_2$, 0.5 mM $MnSO_4$, 1 M betaine, 1×MasterAmp™ RT PCR Reaction Buffer, 10 pmoles of labelled EB-R primer, 10 pmoles of EB-L primer and 1.25 U of RetroAmp™ DNA polymerase was subjected to thermal cycling in an MJ Scientific Minicycler. Cycling conditions were as follows: 60° C. for 20 minutes, 92° C. for 2 minutes; followed by 30 cycles of 92° C. for 1 minute, 55° C. for 1 minute and 73° C. for 1 minute; and the 1 cycle of 73° C. for 4 minutes and a 4° C. hold. After cycling, 5 µl of each RT-PCR reaction was mixed with 1 µl of 10×BESS T-Scan™ Excision Buffer, 1 µl of 200 µg/ml methylene blue and 3 µl of D.I.$H_2$O. This mix was vortexed and placed on a fluorescent light box for 10 minutes. This was followed by the addition of 1 µl of the G excision enzyme mix containing FPG protein and endonuclease IV and an incubation at 37° C. for 30 minutes. The reaction was terminated by adding 5 µl of BESS T-Scan™ Stop/Loading Dye. Each reaction was denatured at 95° C. for 5 minutes and fractionated by 8% denaturing PAGE in a glycerol-tolerant buffer (BESS T-Scan, ™ MasterAmp™ and RetroAmp™ are products from Epicentre Technologies, Madison, Wis.).

The resulting G banding pattern was consistent with the G sequence of standard *E. coli* 16S rRNA gene.

REFERENCES

Bailly, et al., "Delta-elimination in the repair of AP (apurinic/apyrimidinic) sites in DNA," *Biochem. J.* 261:707–713, 1989a.

Bailly, et al., "Mechanism of DNA strand nicking at apurinic/apyrimidinic sites by *Escherichia coli* (formamidopyrimidine) DNA glycosylase" *Biochem. J.* 262:581–589, 1989b.

Blaszyk, et al., "Rapid and efficient screening for p53 gene mutations by dideoxy fingerprinting," *BioTechniques* 18:256–260, 1995.

Breimer, "Enzymatic excision from gamma-irradiated polydeoxyribonucleotides of adenine residues whose imidazole rings have been ruptured," *Nucl. Acids Res.* 12:6359–6367, 1984.

Castaing, et al., "Cleavage and binding of a DNA fragment containing a single 8-oxoguanine by wild-type and mutant FPG proteins," *Nucl. Acids Res.* 2899–2905, 1993.

Cheng, et al., "8-Hydroxyguanine, an abundant form of oxidative DNA damage, caused G to T and A to C substitutions," *J. Biol. Chem.* 267:166–172, 1992.

Chetsanga, et al., "Purification and characterization of Escherichia coli formamidopyrimidine-DNA glycosylase that excises damaged 7-methylguanine from deoxyribonucleic acid," *Biochemistry* 20:5201–5207, 1981.

Chung, et al., "An endonuclease activity of *Escherichia coli* that specifically removes 8-hydroxyguanine residues from DNA," *Mutat. Res.* 254:1–12, 1991.

Deutsch, et al., "Methylene blue adjuvant therapy of schizophrenia," *Clin. Neuropharmacol.* 20:357–363, 1997.

Devchand, et al., "Uracil-DNA glycosylase as a probe for protein-DNA interactions," *Nucl. Acids Res.* 21:3437–3443, 1993.

Floyd, et al., "Methylene blue plus light mediates 8-hydroxyguanine formation in DNA," *Arch. Biochem. Biophys.* 273:106–111, 1989.

Friedman and Brown, "Base-specific reactions useful for DNA sequencing: methylene blue-sensitized photooxidation of guanine and osmium tetroxide modifications of thymine," *Nucl. Acids Res.* 5:615–622, 1978.

Hatahet, et al., "New substrates for old enzymes: 5-hydroxy-2'-deoxycytidine and 5-hydroxy-2'-deoxyuridine are substrates for *Escherichia coli* endonuclease III and formamidopyrimidine DNA N-glycosylase, while 5-hydroxy-2'-deoxyuridine is a substrate for uracil DNA N-glycos lase," *J. Biol. Chem.* 269:18814–18820, 1994.

Hayaski, "PCR-SSCP: a simple and sensitive method Eor detection of mutations in the genomic DNA," *PCR Methods and Applications*, August; 1(1):34–38, 1991.

Keen, et al., "Rapid detection of single base mismatches as heteroduplexes on Hydrolink gels," *Trends in Genetics* 7(1):5, 1991.

Lindahl, "Instability and decay of the primary structure of DNA," *Nature* 362:709–715.

Liu and Sommer, "Restriction endonuclease fingerprinting (REF): A sensitive method for screening mutations in long, contiguous segments of DNA," *BioTechniques* 18 47–477, 1995.

Maxam and Gilbert, "A New Method for Sequencing DNA," *Proc. Natl. Acad. Sci. USA* 74:560–564, 1977.

Myers and Gelfand, "Reverse Transcription and DNA Amplification by a Thermus thermophilus DNA Polymerase," *Biochemistry* 30:7661–7666, 1991.

Negri, et al., "A single-reaction method for DNA secuence determination," *Anal. Biochem.* 197:389–395, 1991.

Negri, et al., "Chemical Method for DNA sequence determination from the 5'-extremity on PCR amplified fragments," *Nucl. Acids Res.* 22:111–112, 1994.

Negri, et al., "One-step, one-lane chemical DNA sequencing by N-methylformamide in the presence of metal ions," *Biotechniaues* 21:910–917, 1996.

Orita, et al., "Detection of polymorphisms of human DNA by gel electrophoresis as single-strand conformation polymorphisms," *Proc. Natl. Acad. Sci. USA* 86:2766–2770, 1989.

Qu, et al., "PCR detection of human papillomavirus: comparison between MY09/MY11 and GP5+/P6+primer systems," *J. Clin. Microbiol.* 35:1304–1310, 1997.

Rodriquez, et al., "Mapping of Copper/Hydrogen peroxide-induced DNA damage at nucleotide resolution in human genomic DNA by ligation-mediated polymerase chain reaction," *J. Biol. Chem.* 270:17633–17640, 1995.

Sanger, et al., "DNA Sequencing with chain-terminating inhibitors," *Proc. Natl. Acad. Sci. USA* 74:5463–5468, 1977.

Sarkar, et al., "Screening for mutations by RNA single-strand conformation polymorphism (rSSCP): comparison with DNA-SSCP," *Nucl. Acids Res.* 20(4):871–878, 1992.

Tchou, et al., "8-Oxoguanine (8-hydroxyguanine) DNA glycosylase and its substrate specificity," *Proc. Natl. Acad. Sci. USA* 88:4690–4694, 1991.

Vaughan and McCarthy, "Glycosylase mediated detection of nucleotide sequences at candidate loci" International application PCT/IE95/00067 (WO 97/03210), 1997.

Vaughan and McCarthy, "A novel process for mutation detection using uracil DNA-glycosylase," *Nucl. Acids Res.* 26:810–815, 1998.

Vennerstrom, et al., "Antimalarial dyes revisited: xanthines, azines, oxazines, and thiazines," *Antimicrob. Agents Chemother.* 39:2671–2677, 1995.

Walker, "Strand Displacement Amplification," In: Novel Amplification Technologies for DNA/RNA-Based Diagnostics, a book presented at a meeting of that name on Apr. 20–22, 1994 in San Francisco, Calif., organized by International Business Communications, Southborough, Mass., 1772–1749.

Watson and Bennett, "Cloning and assembly of PCR products using modified primers and DNA repair enzymes," *Biotechniques* 23:858–864, 1997.

U.S. Pat. Nos.

4,683,195

4,683,202

4,950,665

5,234,809

5,399,491

5,310,652

5,035,996

U.S. Patent Applications

08/534,799

International Applications

WO 95/06752; Shaw and Porter; 3/1995

WO 97/03210; Vaughn and McCarthy; 1/1997

---

We claim:

1. A method of analyzing a DNA molecule, comprising the steps of
   (a) exposing a DNA molecule to an effective amount of a chemical modification reagent, wherein the DNA molecule comprises at least one guanine residue and wherein the reagent converts guanine to 8-hydroxyguanine and wherein an oxidized product is formed,
   (b) exposing the oxidized product to a DNA glycoslyase enzyme in combination with an apurinic/apyrimidinic endonuclease, wherein the N-glycosidic linkage of 8-hydroxyguanine is cleaved, and
   (c) breaking the phosphodiester bond at the 8-hydroxyguanine site and wherein DNA fragments are formed, and
   (d) resolving the DNA fragments by electrophoresis, whereby the position of guanine residues within the DNA molecule is determined.

2. The method of claim 1 additionally comprising the step of synthesizing the DNA molecule of step (a) by exposing a nucleic acid template to conditions wherein the template is replicated.

3. The method of claim 1 additionally comprising the step of synthesizing the DNA molecule of step (a) by amplifying a nucleic acid template by PCR or RT-PCR using at least one labelled PCR primer.

4. The method of claim 1 additionally comprising the step of synthesizing the DNA molecule of step (a) by amplifying a nucleic acid template by PCR or RT-PCR using two differently labelled PCR primers.

5. The method of claim 1 additionally comprising the step of synthesizing the DNA molecule of step (a) by amplifying different nucleic acid templates by PCR or RT-PCR using different labels.

6. The method of claim 1, wherein the chemical modification reagent is a thiazine dye.

7. The method of claim 6, wherein the dye is methylene blue or Taylor's blue (1,9-dimethyl methylene blue).

8. The method of claim 1, wherein the DNA glycoslyase enzyme is FPG protein.

9. The method of claim 1, wherein the apurinic/apyrimidinic endonuclease is endonuclease IV.

10. The method of claim 1, wherein the DNA molecule being analyzed is viral DNA.

11. The method of claim 1, wherein the sequence of guanine residues can be determined on one strand of a DNA molecule.

12. The method of claim 1, wherein the DNA is double-stranded and wherein each DNA strand is labeled with a different dye moiety and the dG sequence of both strands is read in the same lane on a polyacrylamide sequencing gel or a single capillary.

13. A kit for performing the method of claim 1, comprising a means for oxidizing guanine residues and a glycosylase in combination with an apurinic/apyrimidinic endonuclease capable of excising the oxidized residue and cleaving a DNA molecule at the site of oxidation.

14. The kit of claim 13 wherein the oxidation means is a thiazine dye and the glycosylase is FPG protein.

15. The kit of claim 14 additionally comprising PCR primers, a thermostable polymerase and 2'-deoxynucleoside-5'-triphosphates.

16. The method of claim 1 for use in detecting mutations.

17. The method of claim 1 for typing an organism.

18. The method of claim 1 for use in detecting a genetic condition or trait.

* * * * *